(12) United States Patent
Dannaker

(10) Patent No.: US 8,729,108 B2
(45) Date of Patent: May 20, 2014

(54) WATERBORNE TOPICAL COMPOSITIONS FOR THE DELIVERY OF ACTIVE INGREDIENTS SUCH AS AZELAIC ACID

(76) Inventor: Christopher J Dannaker, Monterey, CA (US)

( * ) Notice: Subject to any disclaimer, the term of this patent is extended or adjusted under 35 U.S.C. 154(b) by 1025 days.

(21) Appl. No.: 12/486,625

(22) Filed: Jun. 17, 2009

(65) Prior Publication Data

US 2010/0004296 A1    Jan. 7, 2010

Related U.S. Application Data

(60) Provisional application No. 61/073,102, filed on Jun. 17, 2008.

(51) Int. Cl.
*A61K 31/44*    (2006.01)

(52) U.S. Cl.
USPC ......................................................... 514/355

(58) Field of Classification Search
None
See application file for complete search history.

(56) References Cited

U.S. PATENT DOCUMENTS

| | | | |
|---|---|---|---|
| 3,968,219 A | 7/1976 | Rahtz et al. |
| 4,008,313 A | 2/1977 | Laurent et al. |
| 4,011,322 A | 3/1977 | Rahtz et al. |
| 4,012,510 A | 3/1977 | Wiechert et al. |
| 4,196,203 A | 4/1980 | Kapp et al. |
| 4,196,204 A | 4/1980 | Petzoldt et al. |
| 4,207,316 A | 6/1980 | Schottle et al. |
| 4,292,326 A | 9/1981 | Nazzaro-Porro |
| 4,299,845 A | 11/1981 | Loebenberg et al. |
| 4,330,541 A | 5/1982 | Annen et al. |
| 4,337,311 A | 6/1982 | Petzoldt et al. |
| 4,386,104 A | 5/1983 | Nazzaro-Porro |
| 4,469,684 A | 9/1984 | Huggins et al. |
| 4,670,427 A | 6/1987 | Annen et al. |
| 4,699,924 A | 10/1987 | Durrant et al. |
| 4,713,394 A | 12/1987 | Thornfeldt |
| 4,818,768 A | 4/1989 | Nazzaro-Porro |
| 4,885,282 A | 12/1989 | Thornfeldt |
| 4,946,870 A | 8/1990 | Partain, III et al. |
| 5,089,175 A | 2/1992 | Earnshaw et al. |
| 5,183,925 A | 2/1993 | Heindl et al. |
| 5,187,286 A | 2/1993 | Skuballa et al. |
| 5,196,570 A | 3/1993 | Buchmann et al. |
| 5,385,943 A | 1/1995 | Nazzaro-Porro |
| 5,414,016 A | 5/1995 | Skuballa et al. |
| 5,446,070 A | 8/1995 | Mantelle |
| 5,498,729 A | 3/1996 | Domb |
| 5,502,075 A | 3/1996 | Skuballa et al. |
| 5,545,399 A | 8/1996 | Lee et al. |
| 5,549,888 A | 8/1996 | Venkateswaran |
| 5,608,093 A | 3/1997 | Stache et al. |
| 5,624,943 A | 4/1997 | Heindl et al. |
| 5,686,489 A | 11/1997 | Yu et al. |
| 5,705,144 A | 1/1998 | Harding et al. |
| 5,719,197 A | 2/1998 | Kanios et al. |
| 5,783,602 A | 7/1998 | Skuballa et al. |
| 5,833,998 A | 11/1998 | Biedermann et al. |
| 5,859,054 A | 1/1999 | Skuballa et al. |
| 5,939,082 A | 8/1999 | Oblong et al. |
| 5,972,359 A | 10/1999 | Sine et al. |
| 5,980,921 A | 11/1999 | Biedermann et al. |
| 5,997,887 A | 12/1999 | Ha et al. |
| 5,997,890 A | 12/1999 | Sine et al. |
| 6,001,377 A | 12/1999 | SaNogueira, Jr. et al. |
| 6,133,318 A | 10/2000 | Hart |
| 6,150,403 A | 11/2000 | Biedermann et al. |
| 6,153,177 A | 11/2000 | Bartolone et al. |
| 6,160,012 A | 12/2000 | Buchmann et al. |
| 6,174,533 B1 | 1/2001 | SaNogueira, Jr. et al. |
| 6,238,678 B1 | 5/2001 | Oblong et al. |
| 6,277,892 B1 | 8/2001 | Deckner et al. |
| 6,284,234 B1 | 9/2001 | Niemiec et al. |
| 6,340,706 B1 | 1/2002 | Buchmann et al. |
| H2013 H | 2/2002 | Boyd et al. |
| 6,407,141 B1 | 6/2002 | Hart |
| 6,419,913 B1 | 7/2002 | Niemiec et al. |
| 6,503,523 B2 | 1/2003 | Hoppe et al. |
| 6,534,070 B1 * | 3/2003 | Franke et al. ................. 424/401 |
| 6,551,604 B1 | 4/2003 | Beck et al. |
| 6,562,363 B1 | 5/2003 | Mantelle et al. |
| 6,734,210 B2 | 5/2004 | Hebert |
| 6,787,128 B2 | 9/2004 | Kleen et al. |
| 6,927,206 B2 | 8/2005 | Patt |
| 6,946,124 B2 | 9/2005 | Arnaud-Sebillotte et al. |
| 6,958,327 B1 | 10/2005 | Hillisch et al. |
| 7,008,647 B2 | 3/2006 | Burrell et al. |
| 7,026,308 B1 | 4/2006 | Gavin et al. |
| 7,037,513 B1 | 5/2006 | Traynor et al. |
| 7,109,360 B1 | 9/2006 | Kuenzer et al. |
| 7,169,401 B2 | 1/2007 | Puglia et al. |
| 7,179,789 B2 | 2/2007 | Patt |
| 7,241,456 B2 | 7/2007 | Vromen |
| 7,252,816 B1 | 8/2007 | Angel et al. |
| 7,300,957 B1 | 11/2007 | Whewell |

(Continued)

OTHER PUBLICATIONS

Draelos et al (Therapeutics for the Clinician 76:135-141, 2005).*
www.olay.com (accessed Nov. 15, 2011).*
www.cvs.com (accessed Aug. 27, 2012).*
Jiang, SJ, Zhou XJ. Examination of the mechanism of oleic acid-induced percutaenous peentration enhancement: an ultrastructural study. Biol. Pharm. Bull. 2003; 26:66-68.
Ziel K, Yelverton CB, Balkrishnan R, Feldman Sr. Cumulative irritation potential of metronidazole gel compared to azelaic acid after repeated applications to healthy skin. J Drugs Dermatology. Nov.-Dec. 2005; 4(6): 727-31 Background and Abstract.
Berlex Laboratories. Finacea™ (azelaic acid) gel 15%: US prescribing information. Monteville, NJ, USA, 2003.
Frampton JE, Wagstaff AJ. Azelaic acid gel 15% in the treatment of papulopustular rosacea. Am J Clin Dermatol. 2004; 5(1): 57-64 Abstract.
Draelos, ZD. Effects of azelaic acid 15% gel on skin barrier in rosacea. Cosmet Dermatol. 2008; 21:259-261.

*Primary Examiner* — Craig Ricci
(74) *Attorney, Agent, or Firm* — Blynn L. Shideler; Krisanne Shideler; BLK Law Group

(57) ABSTRACT

A waterborne topical composition is designed specifically to address the treatment of acne vulgaris, rosacea, seborrheic dermatitis and other skin conditions. The composition contains effective amounts of essential components azelaic acid, niacinamide, and glycerin to create a rapidly penetrating and non-irritating compound.

8 Claims, 1 Drawing Sheet

(56) References Cited

U.S. PATENT DOCUMENTS

| | | |
|---|---|---|
| 7,326,408 B2 | 2/2008 | Angel et al. |
| 7,332,152 B2 | 2/2008 | Sanzgiri et al. |
| 7,348,317 B2 | 3/2008 | Chang et al. |
| 2005/0169948 A1 | 8/2005 | Bernstein |
| 2006/0013787 A1 | 1/2006 | Sebillotte-Arnaud |
| 2009/0182054 A1 | 7/2009 | Zhang |

\* cited by examiner

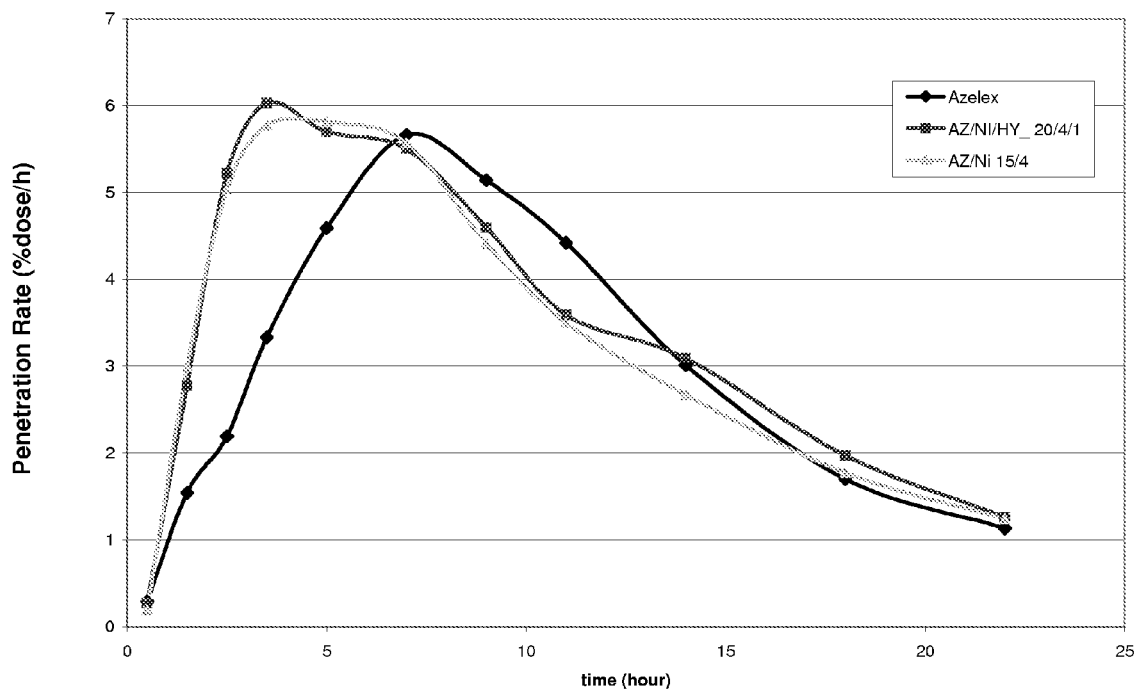

WATERBORNE TOPICAL COMPOSITIONS FOR THE DELIVERY OF ACTIVE INGREDIENTS SUCH AS AZELAIC ACID

RELATED APPLICATIONS

This application claims the benefit of U.S. Provisional Patent Application Ser. No. 61/073,102, filed Jun. 17, 2008, entitled "Moisturizing Vehicles and Aqueous Compositions for the Topical Delivery of Azelaic Acid."

FIELD OF THE INVENTION

The present invention relates to waterborne topical compositions for humans, and more particularly to waterborne topical compositions delivering azelaic acid to the skin. These formulations are suited for treatment of acne vulgaris, rosacea, seborrheic dermatitis, or other skin conditions. Specifically, these formulations result in enhanced and rapid penetration of azelaic acid into human skin and reduced potential for irritant dermatitis. The reduction in irritant dermatitis potential also promotes patient compliance.

BACKGROUND OF THE INVENTION

The term acne comes from a corruption of the Greek ακμή (acme in the sense of a skin eruption). The most common form of acne is known as "acne vulgaris", meaning "common acne". Many teenagers get this type of acne.

Acne vulgaris is a skin disease; caused by changes in the pilosebaceous units (skin structures consisting of a hair follicle and its associated sebaceous gland). Severe acne is inflammatory, but acne can also manifest in non-inflammatory forms. Acne lesions are commonly referred to as pimples, spots, or zits.

Acne is most common during adolescence, affecting more than 85% of teenagers, and frequently continues into adulthood. For most people, acne diminishes over time and tends to disappear, or at least decrease, after one reaches his or her early twenties. There is, however, no way to predict how long it will take for it to disappear entirely, and some individuals will continue to suffer from acne decades later, into their thirties and forties and even beyond.

Acne develops as a result of blockages in follicles. Formation of a plug of keratin and sebum (a microcomedo) is the earliest change. Enlargement of sebaceous glands and an increase in sebum production occur with increased androgen (DHEA-S) production. The microcomedo may enlarge to form an open comedo (blackhead) or closed comedo (whitehead). In these conditions the naturally occurring largely commensual bacteria Propionibacterium acnes can cause inflammation, leading to inflammatory lesions (papules, infected pustules, or nodules) in the dermis around the microcomedo or comedo, which results in redness and may result in scarring or hyperpigmentation.

Rosacea is a common but often misunderstood condition that is estimated to affect over 45 million people worldwide. It affects white-skinned people of mostly north-western European descent, and has been nicknamed the 'curse of the Celts' by some in the British Isles. It begins as erythema (flushing and redness) on the central face and across the cheeks, nose, or forehead but can also less commonly affect the neck and chest. As rosacea progresses, other symptoms can develop such as semi-permanent erythema, telangiectasia (dilation of superficial blood vessels on the face), red domed papules (small bumps) and pustules, red gritty eyes, burning and stinging sensations, and in some advanced cases, a red lobulated nose (rhinophyma). The disorder can be confused and co-exist with acne vulgaris.

Patients with rosacea suffer from redness, stinging, burning and chronic inflammation that results in sensitive skin and intolerance of many topical products. Drugs for treatment of rosacea must ideally be both clinically efficacious and coexist in a vehicle designed for sensitive skin. Most vehicles, such as propylene glycol and fatty acids damage the stratum corneum in order to allow a topical drug to penetrate adequately.

There are a variety of compositions available for treating inflammatory acne vulgaris and rosacea, including topical and systemic antibiotics and retinoids. Azelaic acid, or nonanedioic acid, has been used to effectively treat acne. However, at higher concentrations, particularly at prescription strength, azelaic acid may be irritating to skin. At lower concentrations, effectiveness of the acid is compromised. Carriers such as alcohols added to enhance absorption of the acid at lower concentrations may cause drying of the skin and hence additional irritation. It would be desirable to provide an effective treatment composition for acne vulgaris and rosacea that is non-irritating and non-drying yet allow for effective release of azelaic acid from the vehicle and subsequent rapid penetration into the skin.

Ideal topical drugs for rosacea should not damage the skin barrier function and enhance hydration while allowing such difficult-to-dissolve drugs as azelaic acid to be solubilized and bioavailable.

In an attempt to increase penetration of azelaic acid into skin, formulations containing hydrogels consisting of triglyceride, propylene glycol, at least one polysorbate, polyacrylic acid and soy lecithin have been devised. These vehicles deliver more azelaic acid into the skin than the prior art. Despite greater penetration into the skin, formulations with 15% azelaic acid (Finacea™) utilizing this patented vehicle have been found to be significantly more irritating when compared to other rosacea topical treatments such as metronidazole 0.75%.

Patient compliance is very important to the success of medical treatment. In diseases such as rosacea, acne, and seborrheic dermatitis, there exists heightened skin sensitivity. In a study by the manufacturer of azelaic acid 15% gel (Finacea™) for rosacea; over 30% of treated patients complained of burning, stinging or tingling. This side effect would be expected to significantly and negatively impact patient compliance. Ideally, a vehicle should not only effectively deliver azelaic acid to the skin but should do so rapidly in order to minimize irritation and hypersensitivity.

There is a need for delivery of effective concentrations of azelaic acid to the skin while minimizing irritation. The present invention allows for enhanced delivery of azelaic acid while minimizing irritation, thus encouraging optimal patient compliance.

SUMMARY OF THE INVENTION

A waterborne topical composition for the enhanced penetration of azelaic acid into human skin in the treatment of acne vulgaris, rosacea and other skin conditions is provided. The composition comprises effective amounts of azelaic acid, niacinamide, and glycerin.

BRIEF DESCRIPTION OF THE FIGURE

FIG. 1 illustrates percutaneous penetration of compositions of the present invention as compared to the prior art.

DETAILED DESCRIPTION OF THE PREFERRED EMBODIMENTS

Other than in any operating examples, or where otherwise indicated, all numbers expressing quantities of ingredients, reaction conditions and so forth used in the specification and claims are to be understood as being modified in all instances by the term "about." Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

As used in this specification and the appended claims, the articles "a," "an," and "the" include plural referents unless expressly and unequivocally limited to one referent.

The various embodiments and examples of the present invention as presented herein are each understood to be non-limiting with respect to the scope of the invention.

The compositions of the present invention are waterborne. They may be prepared in the form of a liquid, cream, gel, fluid, lotion, emulsion or microemulsion as desired. Viscosity of the composition may be altered using any of various formulating methods, such as by changing the amount of carrier medium.

The composition of the present invention contains effective amounts of essential components azelaic acid, niacinamide, and glycerin.

Azelaic acid (nonanedioic acid) is a saturated dicarboxylic acid found naturally in wheat, rye, and barley. It is a natural substance that is produced by *Malassezia furfur* (also known as *Pityrosporum ovale*), a yeast that lives on healthy skin. Azelaic acid is typically present in the composition of the present invention in amounts up to 20 percent by weight. In prescription strength formulations of the composition, azelaic acid is present in an amount typically of at least 4 percent by weight. In countries other than the United States, azelaic acid may be allowed in over the counter (OTC) formulations and typically contain azelaic acid at less than 4 percent by weight.

Azelaic acid is only slightly soluble in water, cosmetic oils and alcohols; thus each of these solvents has conventionally had limitations as a carrier for topical formulations containing azelaic acid. For example, an aqueous solution of azelaic acid would contain a maximum of about 0.24% by weight (w/w) azelaic acid, which is not enough to be effective. Azelaic acid has little or no solubility in cosmetic oils. Alcohols are unsatisfactory in high concentrations as they have the undesirable side effect of drying and irritating the skin.

Niacinamide, also known as nicotinamide and nicotinic acid amide, is the amide of nicotinic acid (vitamin $B_3$). Nicotinamide is a water-soluble vitamin and is part of the vitamin B group. Typically the niacinamide is present in an amount of up to 10 percent by weight in the composition of the present invention. Though not intending to be bound by theory, it is believed that the combination of azelaic acid and niacinamide in the composition of the present invention surprisingly offers greater therapeutic benefits than either component used alone. Azelaic acid is believed to enhance the penetration and effect of niacinamide. In turn, the effect of azelaic acid on follicular inflammatory conditions such as acne rosacea is enhanced by the niacinamide. It is believed that this effect is due in part to increased aqueous solubility of dicarboxylic acids such as azelaic acid in the presence of niacinamide. Niacinamide in combination with cyclodextrin was noted to act as a solubility enhancer of metronidazole. See U.S. Pat. No. 7,348,317

In certain embodiments of the present invention, the niacinamide is present in an amount at least sufficient to enhance penetration of the azelaic acid into skin. Niacinamide may be used in combination with nicotinic acid in the composition of the present invention; usually, however, the composition is essentially free of nicotinic acid. By "essentially free" is meant that if the material is present in the composition, it is present incidentally in an amount less than 0.1 percent by weight, preferably less than trace amounts.

Glycerin is a chemical compound also commonly called glycerol or glycerine. It is a colorless, odorless, viscous liquid. Glycerin is a sugar alcohol, and has three hydrophilic alcoholic hydroxyl groups that are responsible for its solubility in water and its hygroscopic nature. Typically, the glycerin is present in the composition of the present invention in an amount of up to 10 percent by weight. Glycerol has been found to enhance penetration of monoazelate esters into the skin. It is proposed in U.S. Pat. No. 7,300,957 that glycerin esterified with azelaic acid enhances the percutaneous penetration of azelaic acid into the skin, after which the glycerin disassociates. Unexpectedly, it has been found that this process does not necessarily require the prior esterification of azelaic acid with glycerol to form glycerol monoazelate. Compositions of the present invention are essentially free of azelaic acid esters, including reaction products of azelaic acid and glycerin.

Aquaporins are fairly newly-discovered "channels" in biological tissues such as skin that allow for the passage of certain molecules into cells to enhance cellular hydration. Aquaporins are integral membrane proteins from a larger family of major intrinsic proteins (MIP) that form pores in the membranes of biological cells. They compose six trans-membrane alpha helical structures arranged in a right-handed bundle and form tetramers in the cell membrane. The main aquaporin in the epidermis is-known as aquaporin-3 also known as aquaglyceroporin. Aquaporin-3 controls water transport in addition to movement of glycerol, $CO_2$, ammonia and urea. Aquaporin-3 expression is increased in human skin diseases with elevated transepidermal water loss such as rosacea. Not intending to be bound by theory, it is believed that glycerin in the composition of the present invention allows for enhanced absorption of the active ingredients into the skin through aquaporins as well as function as hydrators of the skin to minimize the potential for skin irritation from azelaic acid.

The topical composition of the present invention may optionally contain additional components as active ingredients or as inert additives. For example, the composition of the present invention may further comprise hyaluronic acid and/ or a derivative thereof. Other suitable components include alcohols such as cetyl alcohol, stearyl alcohol, and benzyl alcohol, surfactants such as sodium lauryl sulfate, isopropyl palmitate, sorbitol, and lactic acid. Mixtures of these components are often used. Sunscreens may be used in combination with other ingredients in the composition of the present invention; usually, however, the composition is essentially free of sunscreens.

A particular example of a waterborne topical composition in accordance with the present invention has the following composition: 5 percent by weight azelaic acid, 4 percent by weight niacinamide, 5 percent by weight cetyl alcohol, 2.5 percent by weight stearyl alcohol, 0.83 percent by weight sodium lauryl sulfate, 1.67 percent by weight isopropyl palmitate, 8.33 percent by weight glycerin, 8.33 percent by weight sorbitol, 0.83 percent by weight lactic acid, and 1.37 percent by weight benzyl alcohol in water.

It is recognized that the present commercially available azelaic acid topicals (Azelex™, Finacea™) commonly cause skin irritation. This is due in part to irritant dermatitis induced by azelaic acid as delivered by present vehicle technology.

Although topical products in aqueous bases have been used to emulsify azelaic acid (U.S. Pat. No. 6,734,210); these products either penetrate poorly into the skin or demonstrate significant irritation.

The proposed formulation of the present invention demonstrates superior, rapid skin penetration using an in vitro human skin model when compared to the prior art. It allows for larger amounts of pharmaceutical active ingredient to penetrate living skin layers. The rate of penetration (% dose/hr) is nearly 3× that of azelaic acid-cream according to prior art.

The compositions of the present invention are also relatively non-irritating and as such promote patient compliance. In a series of 30 test subjects a cream made of 20% azelaic acid in this optimized vehicle was applied to the forearm twice daily for two weeks. No patients complained of burning, stinging, irritation, or erythema throughout the pilot study. After two weeks a visual inspection of the forearm area was performed by a board certified dermatologist. The examining physician noted an absence of redness, irritation or scaling in the applied area. Twenty patients with active rosacea were randomized to receive either active test cream consisting of 15% azelaic acid in the optimized vehicle described or vehicle cream alone. After six weeks of use, the treated areas were examined and all found to be free of clinical irritation.

The examples given herein below illustrate the preparation of azelaic acid with an optimized vehicle that contains niacinamide and glycerin. Only a few of the many possible embodiments that may be anticipated are shown by these examples which are intended to define, in a non-limiting sense, the scope encompassed by the invention.

EXAMPLES

The effect of three different formulations on the skin disposition of radiolabeled azelaic acid was observed. This was evaluated using excised human skin in an in vitro flow-through diffusion cell system. Example 1 is comparative; Examples 2 and 3 are in accordance with the present invention.

Materials and Methods

Radiolabeled Test Substance:
Chemical Name: [1-$^{14}$C]-azelaic Acid

Supplier: ARC (American Radiolabeled Chemicals, Inc., 101 ARC Drive, St. Louis, Mo. 63146
Radiochemical purity and specific activity: 99%, 50 mCi/mmole (Appendix A)
Stability: Expected to be stable under the conditions of storage and use
Storage: 0-5° C.
Amount supplied: 0.050 mCi of $^{14}$C label Formulations Example 1 (Comparative): Azelex™ 20% cream formulation
Example 2: Azelaic Acid/Niacinamide (AZ/NI) 15/4%
Example 3: Azelaic Acid/Niacinamide/Hyaluronic Acid (AZ/NI/HY) 20/4/1% cream formulation
Formulations were stored at room temperature.
Procedure for Addition of Radiolabel:
$^{14}$C-azelaic Acid was received on Oct. 7, 2008. The sample was received as an ethanolic solution containing 50 µCi in 0.5 ml. The source was stored at 0-5° C. On the same day, formulations were spiked with the radiolabel. For each formulation, 10 µCi (100 µl) of the source was transferred to a 2×2 inch glass plate and the ethanol allowed to evaporate. Twenty µl of distilled water was added to the plate and mixed into the label with a stainless steel spatula. Five hundred mg of formulation was added in portions to the plate and mixed (spatulated) with the radiolabel. After thorough spatulation, formulations were transferred to 2 ml glass vials with Teflon® lined caps. All formulations were stored at room temperature and there was no unused radiolabeled azelaic acid.
Procedure:
Full-thickness normal human abdominal skin was collected as a surgical specimen from a 34-year-old white female on Jul. 1, 2008, and shipped overnight on gauze/RPMI at wet ice (non-frozen) temperature. The sample was received on Jul. 2, 2008, and was immediately frozen at −20 to −25° C. The sample was maintained at this temperature in a monitored laboratory freezer. On the morning of Oct. 8, 2008, the skin sample was allowed to thaw to room temperature and 2×8 inch strips were dermatomed (Brown Electrodermatome) to a thickness of 0.3-0.5 mm. Circles of skin, approximately 1 inch in diameter, were cut from the strips and placed on stainless steel skin diffusion cells (total of 15 cells) mounted in temperature control blocks connected to circulating water baths at 37° C. A small donor chamber, approximately 3 ml in volume, was clamped to the stratum corneum side of the skin, so that the skin surface was open to the laboratory atmosphere. RPMI tissue culture medium containing gentamycin sulfate perfused the penetration cell (Watson-Marlow or Ismatec peristaltic pumps) at a flow rate of approximately 1.5-2.0 ml/h. Since the dead space of the diffusion cell was 0.3 ml, this gave 5-7 cell volumes of receptor fluid each hour. After determining that no visible leaks were present, a tritiated water skin integrity test was performed (Stratacor SOP SPE.7 Revision 4.00). This test was done over a 3-hour period. All skin samples on the cells passed the skin integrity test.

On the afternoon of Oct. 8, 2008, approximately 10 mg of each of the 5 formulations was transferred to the stratum corneum of each of the 15 diffusion cell, so that each formulation was replicated 3 times. Formulations were transferred to the head of a small glass applicator, shaped like a small glass nail, with the closed end of a capillary melting point tube. The mass of the formulation was determined on a tared semi-micro balance (0.01 mg readable). After application to the skin, the glass applicator was reweighed to determine the exact amount of each formulation that was transferred to the skin samples.

The applied dose for each skin sample was determined by multiplication of the mass transferred and the specific activity of the formulations.

The skin disposition of radiolabeled azelaic acid in five different formulations was evaluated on frozen human skin obtained from a single donor following elective surgery. Three replicates were obtained for each formulation, requiring 15 skin samples.

Excised full-thickness human skin was cut with a dermatome to yield a thickness of 0.3-0.5 mm. This "split-thickness" skin was composed of the epidermis (100 µm in thickness) and the outer most portion of the dermis containing the papillary dermis. The stratum corneum portion of the epidermis is approximately 10 µm in thickness.

Circles of split thickness skin were sandwiched between the skin attachment surface of stainless steel flow-through diffusion cells and glass donor chambers. Number 15 Thomas clamps held the assemblies together. The diffusion cells were placed in temperature controlled holders. Water at 37° C. circulated through the cell holders. RPMI tissue culture medium, prewarmed to 37° C., perfused the penetration cell at a flow rate of 1.5-2.0 ml/h. Outflow from the penetration cells was collected in Liquid scintillation vials (LSC) in a fraction collector (ISCO Retriever IV). The fraction collector was controlled by a programmable laboratory controller, so that 4 of 1 hour samples, 4 of 2 hour samples, and 3 of 4 hour samples were collected after the $^{14}$C-labeled formulations were in place.

Twenty-four hours after application, radiolabeled penetrant present in the tissue culture medium in the LSC vials was mixed with LSC fluid (Perkin-Elmer Ultima Gold) for radiometric analysis. Fluid remaining in the cells and tubing was pumped into a separate vial (final volume) and processed as for the timed fractions. The Thomas clamps were removed from the donor chambers and the donor chambers were wiped and the wipes assayed for radioactivity. The skin disks were removed from the penetration cells and the cells wiped and wipes assayed for radioactivity. The skin disks were positioned on a cork board protected with plastic film. The skin disks were held in place with 4 pins situated on the perimeter of the disk at "12 noon", "3 o'clock", "6 o'clock" and "9 o'clock". The skin surface was decontaminated with two tape strips (3M Magic® tape), which were placed in LSC vials along with 1-2 ml of tetrahydrofuran. After allowing a time period for dissolution of the tape strips (48-72 hours), LSC fluid was added to the vials for radiometric assay. Pins were removed and a plastic film was placed over the skin sample. A weight, preheated to 65° C., was placed on top of the skin and remained in place for 90 seconds. The plastic film was removed from the skin surface and placed in a LSC vial for radiometric assay. The epidermis was peeled away from the dermis, and each layer was placed in separate glass LSC vials. After adding tissue solubilizer (Solene 350, Perkin-Elmer), the vials were gradually warmed to facilitate dissolution. After allowing a time period of 24 hours for dissolution, LSC fluid was added to each vial for radiometric assay. The film directly under the skin sample was placed in an LSC vial for radiometric assay.

Samples were counted on a Perkin Elmer A2300 liquid scintillation counter equipped with temperature control, chemiluminescence correction and static controller. Samples were counted for 2 minutes on a dual label protocol, since tritium was used in the preliminary skin integrity test and C-14 was used in the radiolabeled formulations.

Analyses were performed using BMDP statistical software. One way analysis of variance was conducted to determine the effect of formulation on the distribution of radioactivity on the skin surface tape strips, epidermis, dermis and total receptor fluid. When a significant F was observed, the Student-Newman-Keuls multiple range test was applied to determine which formulations were different. All analyses were conducted at the 0.05 level of significance.

Results

The disposition of radioactivity (percent of applied radioactive dose) following topical application of labeled azelaic acid in three formulations was determined.

Average mean recoveries ranged from 90 to 99% at 24 hours, providing confidence that mass balance was achieved in the study. Approximately 400,000 dpm (0.2 µCi) were applied to each cell, and the majority of that radiolabel was recovered from the receptor fluid (70-80%) The skin surface tape strips accounted for the majority of the remaining label (6-20%) and only low percentages (1-3%) were recovered from the epidermis or dermis at 24 hours. Radiolabel contained in the dermis and receptor fluid was summed to give an estimate of in vivo dermal absorption.

For all the formulations, the vast majority of topically applied azelaic acid penetrated completely through the skin and into the receptor fluid (70-80%) at 24 hours. Only 1-3 percent of the applied dose remained in the epidermis or dermis and the differences between formulations were small. When the rate of penetration was graphed, significant differences between the test creams and the Azelex™ control were noteworthy. Both test formulations' initial penetration rates were superior to Azelex™ and in particular, they reach a maximum flux about two hours sooner than Azelex™. The compositions of the present invention typically demonstrated a penetration rate of at least 5% active ingredient/hr, within 2.5 hours of application to human skin.

Since in real life, formulations tend to get rubbed off or lost by stratum corneum exfoliation post application, having a higher initial penetration rate is important to getting higher levels in the skin.

Utilizing radiolabeled azelaic acid on human skin, it was found that the formulation of the present invention unexpectedly and significantly enhanced the rate of penetration of azelaic acid. The present formulation demonstrated vastly superior penetration dynamics when compared to the industry standard, Azelex™. The graph (FIG. 1) demonstrates rapid percutaneous penetration of compositions of the present invention in the first one to two hours when compared to Azelex™. Nearly a three-fold increase in penetration (6%/hr) was reached by the test formulation compared to less than 2%/hr penetration of Azelex at the two hour time frame. Over a three-fold increase in penetration rate in the critical 1-2 hour time after topical application is shown.

What is claimed is:

1. A waterborne topical composition for the treatment of acne vulgaris, rosacea, seborrheic dermatitis or other skin conditions comprising effective amounts of azelaic acid, niacinamide, and glycerin, and wherein the composition demonstrates a penetration rate of at least 5% active ingredient/hr, within 2.5 hours of application to human skin, wherein the azelaic acid is present in an amount of at least 4 percent by weight and the glycerin is present in an amount of up to 10 percent by weight, and wherein the waterborne composition is in the form of one of a liquid, emulsion and microemulsion.

2. The waterborne topical composition of claim 1 wherein the azelaic acid is present in an amount of up to 20 percent by weight.

3. The waterborne topical composition of claim 1 wherein the niacinamide is present in an amount of up to 10 percent by weight.

4. The waterborne topical composition of claim 1 wherein the composition is essentially free of azelaic acid esters.

5. The waterborne topical composition of claim 1 wherein the niacinamide is present in an amount of at least 4 percent by weight.

6. The waterborne topical composition of claim 5 wherein the azelaic acid is present in an amount of up to 20 percent by weight.

7. The waterborne topical composition of claim 6 wherein the niacinamide is present in an amount of up to 10 percent by weight.

8. The waterborne topical composition of claim 7 wherein the composition is essentially free of azelaic acid esters.

* * * * *